United States Patent [19]

Labbe et al.

[11] Patent Number: 4,944,659
[45] Date of Patent: Jul. 31, 1990

[54] IMPLANTABLE PIEZOELECTRIC PUMP SYSTEM

[75] Inventors: Jean-Marie Labbe; Eduard H. J. Damhuis, both of Bousval, Belgium; Robert E. L. Cox, Le Pecq, France

[73] Assignee: KabiVitrum AB, Stockhol, Sweden

[21] Appl. No.: 282,131

[22] PCT Filed: Jan. 27, 1988

[86] PCT No.: PCT/EP88/00062
§ 371 Date: Nov. 22, 1988
§ 102(e) Date: Nov. 22, 1988

[87] PCT Pub. No.: WO88/05314
PCT Pub. Date: Jul. 28, 1988

[30] Foreign Application Priority Data

Jan. 27, 1988 [GB] United Kingdom .......... 8701731

[51] Int. Cl.⁵ .................. A61M 1/00; F04B 17/00
[52] U.S. Cl. .................. 417/322; 310/26; 604/151
[58] Field of Search .......... 417/322, 413; 310/26; 604/131, 151, 891.1

[56] References Cited

U.S. PATENT DOCUMENTS

| 4,360,019 | 11/1982 | Portner et al. | 604/151 |
| 4,487,603 | 12/1984 | Harris | 604/891.1 |
| 4,496,343 | 1/1985 | Prosl et al. | 604/131 |
| 4,596,575 | 6/1986 | Rosenberg et al. | 604/891.1 |
| 4,604,090 | 8/1986 | Reinicke | 604/131 |
| 4,619,653 | 10/1986 | Fischell | 604/151 |

FOREIGN PATENT DOCUMENTS

| 0200083 | 11/1984 | Japan | 417/413 |
| 0203889 | 11/1984 | Japan | 417/413 |

OTHER PUBLICATIONS

Spencer, W. J. et al., "An Electronically Controlled Piezoelectric Insulin Pump and Valves", May 1978, IEEE Transactions on Sonics and Ultasonics, vol. SU-25, No. 3, pp. 153-156.

*Primary Examiner*—Leonard E. Smith
*Assistant Examiner*—David W. Scheuermann
*Attorney, Agent, or Firm*—Pollock, Vande Sandy & Priddy

[57] ABSTRACT

A dispensing device for use in an implantable drug delivery system for ambulatory patients comprises a pump in a drug reservoir and a piezoelectric disc element bonded to a diaphragm member forming one wall of a pump chamber and a battery and electrical circuits for cyclically applying electrical voltage to the piezoelectric member for inducing pumping movement in the diaphragm member to pump drugs from a reservoir via a valve and to a delivery catheter via another valve. A gas spring is provided to move the pump to maintain adequate pressure in the drug reservoir.

9 Claims, 3 Drawing Sheets

IMPLANTABLE PIEZOELECTRIC PUMP SYSTEM

BACKGROUND OF THE INVENTION

This invention relates to pumps of a small size particularly though not exclusively implantable pumps which are sufficiently small for use within the human body.

Pumps of small dimensions are used in implantable drug dispensing divices where a medicament is to be dispensed to an ambulatory patient on a regular or intermittent basis over an extended period of time, as where insulin is dispensed in the treatment of diabetes, or where chemotherapeutic drugs are dispersed in the treatment of cancer. In these circumstances it is advantageous in the treatment with the drug to perform an automatic dispensation of the drug without having to rely upon pills or injections. Thus a unit is implated within the patient comprising a reservoir of the drug and a pump, the pump being under control of a control circuit which may be coupled by an electromagnetic transmitter and receiver to an external control source.

Such a device for delivering the drug must be reliable in operation, sealed against body fluids and must hold a sufficient quantity of medication so as to avoid the need for frequent refills and must be refillable when empty. Furthermore, such dispensing systems must be physically small so as to be readily implatable without unnecessary disturbance of the body.

It is known to employ in such dispensing devices pumps such as the peristaltic type or solenoid type. Peristaltic pumps operate by responding to blood pressure within the body and solenoid pumps operate under control of an internal battery connected to a solenoid for operating a suitable pump mechanism. However such pumps are relatively large, and considering their size, are inefficient within the context of implantable units.

SUMMARY OF THE INVENTION

The present invention is based on the concept of a pump which incorporates a mechanism which is actuated by means or a piezoelectric element. Such a pump can be made of a very small size and is therefore suitable for use in an implatable drug delivery system. However, such a pump may be of use in whatever application where the requirement is for a pump of very small size.

The present invention therefore provides in general terms a pump comprising a source of electric power connected to means for cyclically applying electrical voltage to a piezoelectric element for inducing periodic changes in dimension in the piezoelectric element, the piezoelectric element, being physically contiguous with and directly coupled to a movable pump element whereby changes in dimension of the the piezoelectric element induce pumping movement into the movable pump member.

Thus, since all that is required to provide the pump motive power is a piezoelectric element and a source of electrical power, such as for example a battery, and since the piezoelectric element is contiguous with and directly coupled with the movable pump element with no intervening shaft or push rod, the piezoelectric pump may be made very small in dimensions.

The electrical power supplied to the piezoelectric element from the battery may be in pulsed d.c. form or alternatively and as preferred for efficiency it may be AC, with a suitable inverter circuit being provided.

The movable pump member may be of any suitable type, rotatable or displaceable, and the piezoelectric element may be coupled to the pump member in such a way as to induce the required type of movement. In a preferred embodiment, the movable pump member comprises a flexible membrane, movement of which increases or decreases the size of the pump chamber, which is coupled to a drug reservoir and an outlet port by suitable one way valves. Thus a decrease in volume of the pump chamber causes a drug within the pump chamber to be expelled through the valve of the outlet port, the valve at the inlet port remaining closed, whereas when the volume of the pump chamber is increased by movement of the membrane, the one way valve at the outlet port is closed whereas the one way valve at the inlet port is opened to permit further drug to be introduced into the pump chamber. As preferred, the piezoelectric element comprises a planar element extending over a substantial or major part of the surface area of the membrane and being firmly affixed to the surface thereof. Thus when dimensional changes are induced in a suitable direction in the piezoelectrical element, this causes the piezoelectric element to curve in one or two opposite directions from the plane in which it is disposed and the consequent bowing effect of the element causes a corresponding deformation of the membrane resulting in similar type of movement of the membrane. Thus the pump may be configured as essentially a flat disc-like element, with the piezoelectric element, the membrane forming the movable pump member and the pump chamber, all being of essentially planar form.

A preferred embodiment of the invention will now be described with reference to the accompanying drawings wherein:

BRIEF DESCRIPTION OF THE PREFERRED EMBODIMENTS

Figure 1:
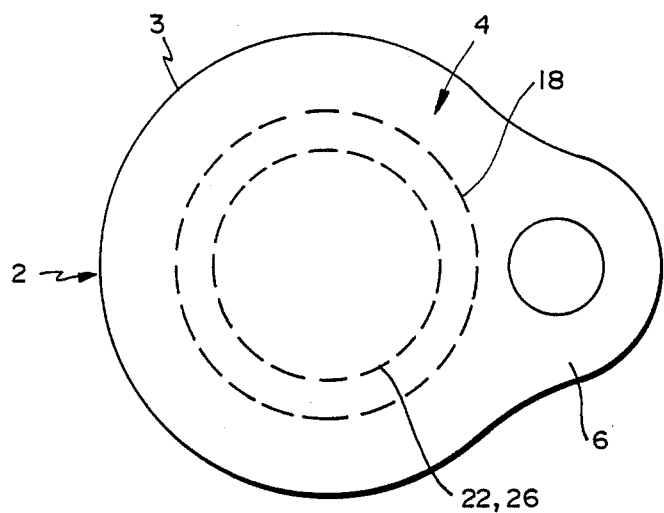
FIG. 1 is a view in elevation of the exterior of an implantable dispenser incorporating a pump according to the invention.

Referring now to the drawings, there is shown an implantable dispenser 2 for use in a drug delivery system where the dispenser is implanted into the body of a human being and is operative to dispense into the body suitable quantities of a drug at intervals under control of a circuit whithin the dispenser and as required under external control by means of a receiver/transmitter arrangement. The dispenser 2, as shown in FIG. 1, comprises an outer casing 3 of bio-compatible material, for example titanium alloy or stainless steel or biologically compatible silicone rubber. The dispenser body comprises a main portion 4 which is circular in elevation with a diameter of 3.5 cm (this dimension and the dimensions quoted below are approximate). The depth of the main portion 4 is 2.5 cm. A lobe portion 6 is provided having a width as measured from the circumference of the circular portion 4 of 1.5 cm and having a depth of 1.5 cm.

Figure 2:
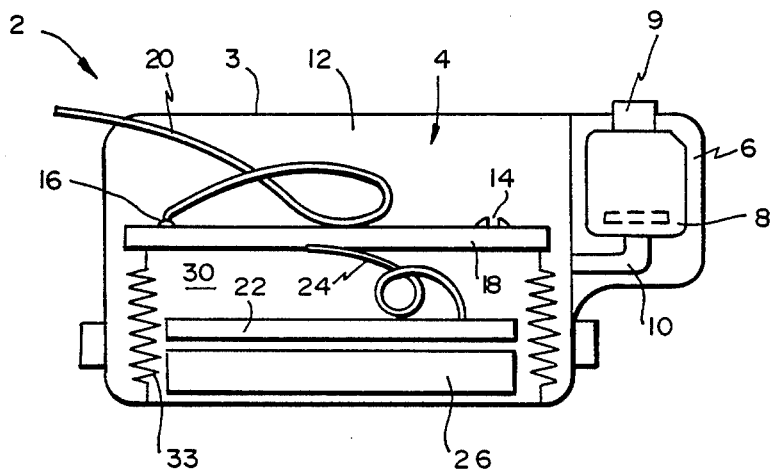
FIG. 2 is a schematic cross-sectional view of the dispenser of FIG. 1.
Figure 3A:
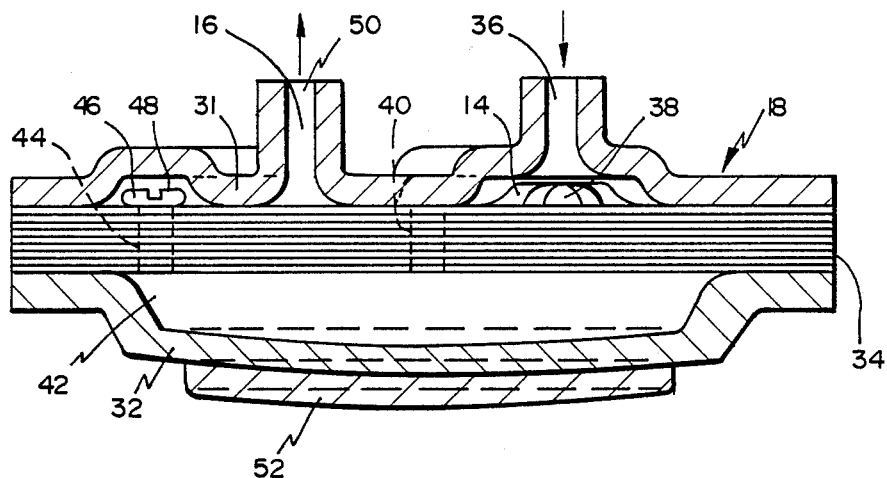
FIG. 3a is a view in cross-section of the pump of the implantable dispenser with both valves down.
Figure 3B:
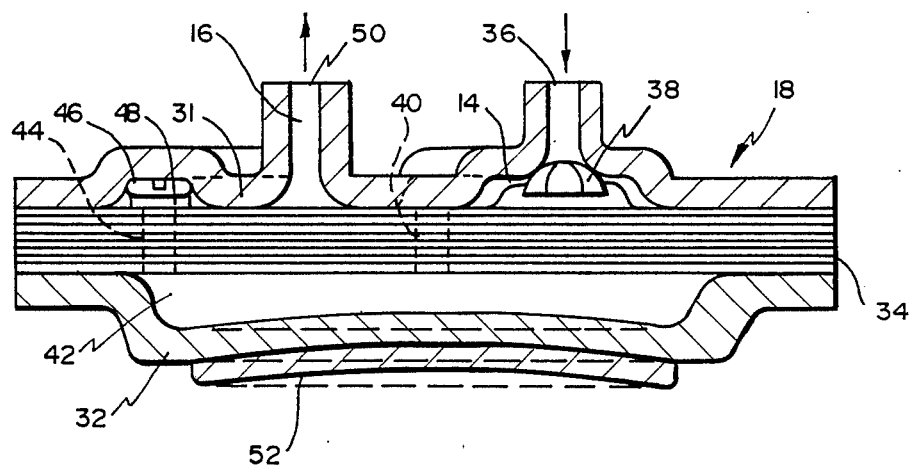
FIGS. 3b is a view in cross-section of the pump of the implantable dispenser with both valves up.

The overall configuration of the implantable dispenser is shown in FIGS. 2 and 3a and 3b as comprising a septum 8 mounted in lobe portion 6 and containing a radially compressed block of silicone rubber, an inlet 9 being provided for external access and a passageway 10 to a main drug reservoir region 12. In use, the reservoir 12 is filled by insertion of the hypodermic needle of a syringe into the silicone rubber insert via a passageway 9, so that the drug flows into the main reservoir region 12 via a passageway 10. Extraction of the needle, when the reservoir is filled, automatically closes the silicone block. Valves 14, 16 are provided with, inlet value 14 permitting entry of the drug into a pump 18 and outlet value 16 permitting exit of the drug from the pump body to a delivery catheter 20, which extends from the dispenser body to a suitable location within the human body. The pump is connected to an electronic control circuit by means of electrical leads 24, the electronic circuit being powered by a battery 26. A gas spring is provided in the area 30 between the pump and the electronic circuit 22 within the volume enclosed by a bellows 33. The function of the gas spring is to maintain an essentially constant pressure in reservoir 12 as the quantity of drug decreases during infusion. By selecting a suitable mixture of "Freon"-type hydrocarbons, which liquify at about one bar pressure, the pressure in the gas spring can be made to remain effectively constant (apart from the spring characteristics of the bellows) as the drug is used up and the bellows 33 opens.

The pump is shown in more detail in FIGS. 3a and 3b as being of generally flat and planar shape being 3.0 cm in diameter and 2 mm thick. The pump comprises two plate members 31, 32 of pressure molded titanium alloy and an intermediate plate 34 is also formed of titanium alloy. These plates define a port 36 for inlet valve 14 housing a freely movable valve member 38 and communicating with a passageway 40. Passageway 40 formed in intermediate plate 34 communicates with a pump chamber 42 and a further channel 44 formed in plate member 34 communicates with an outlet valve having a freely movable valve member 46 which is mounted in a recess 48 which communicates with outlet 50.

Titanium plate 32 defines a movable member to which is bonded a circular plane piezoelectric sheet 52. Suitable seals are provided (not shown) surrounding the valve members, the seals and valve members being made of biologically compatible materials, for example silicone rubber. The three plates 31, 32, 34 are sealed together by a technique such as electron beam welding or diffusion bonding. The piezoelectric element 52 is mounted on plate 32 using a conductive epoxy filled with silver.

In operation, when an electric voltage is applied across the thickness of the piezoelectric element 52, this creates a bowing, resulting in the central part of piezoelectric element moving out of the plane of the element a certain amount whereby a corresponding deformation in plate 32 and thus causing an expansion or contraction of volume of the pump chamber. Where expansion is caused, this creates a suction effect causing valve member 38 to be moved downwardly allowing drug from reservoir 12 to flow into the valve chamber. Outlet valve member 46 is maintained against passage 44 during this movement. Upon contraction of the space of the pump chamber caused by inward movement of plate 32, valve member 46 is pushed upward by permitting a drug to flow through the outlet valve 16.

Figure 4:
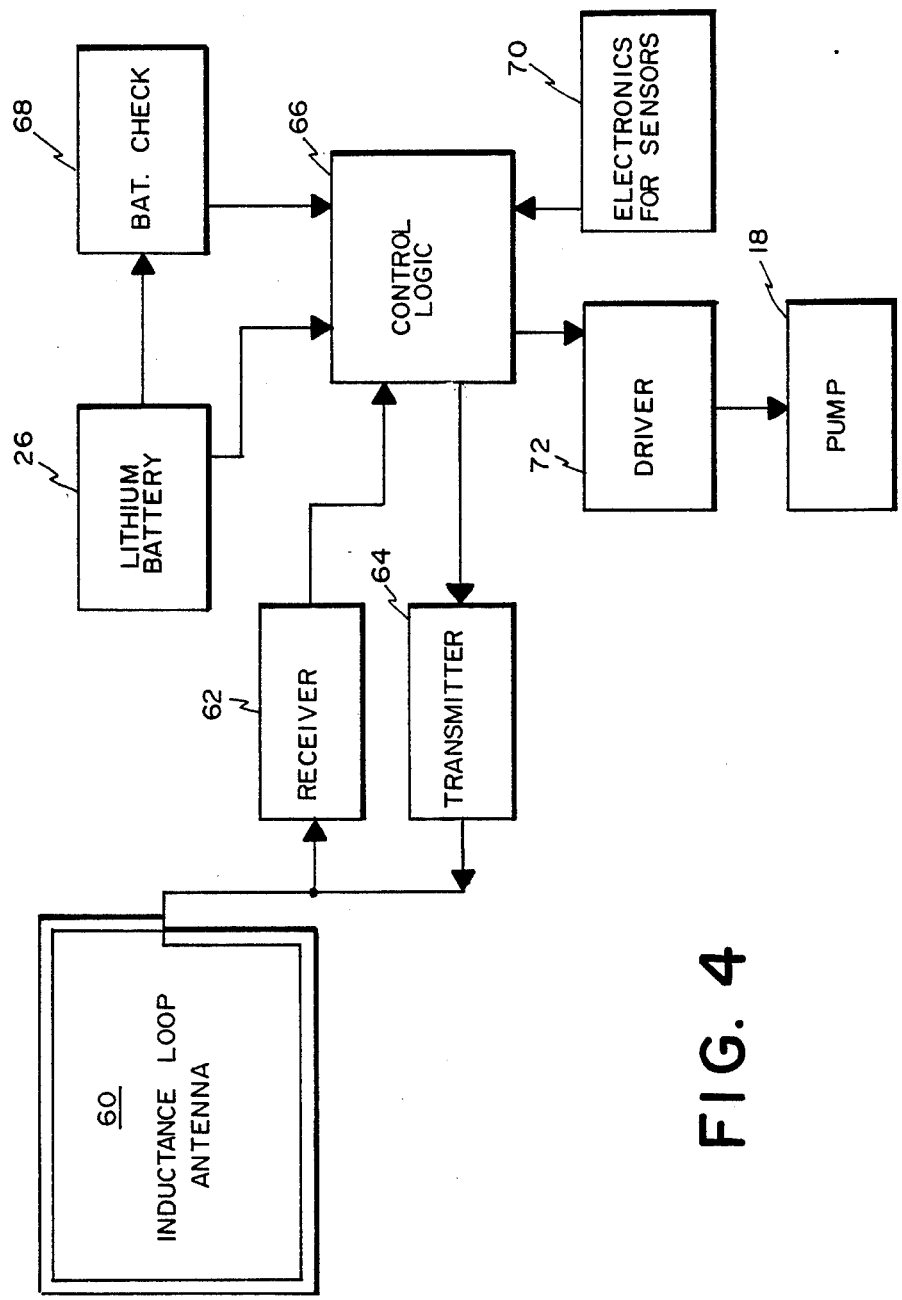
FIG. 4 is a block diagram of the electrical control circuit of the implantable dispenser.

Referring now to FIG. 4 there is shown the electronic circuitry for controlling the pump comprising an inductive loop antenna 60 which receives electrical signals from external control apparatus. This is connected to a receiver and transmitter 62, 64 which in turn provide and receive signals from a central control logic 66. A lithium battery 26 is coupled via a battery checking circuit 68 to control logic 66. Electronics circuits 70 are provided, coupled to sensors which are situated within the pump to monitor conditions, such as battery charge, critical operating voltages, internal humidity, pump/valve monitoring, quantity of drug in reservoir and rate of dispensation, clock settings and stored operating system. In addition sensors may be situated at parts of the human body to determine from biological conditions whether a drug should be administered. The control logic is also coupled to an oscillatory driver 72 which includes an inverter circuit and which provides alternating current to the pump for causing a pumping action of the pump. It may thus be seen that the pump can be controlled in any suitable manner to provide a regular or intermittent flow or drug to a person having this dispenser device implant-therewithin, the pump being controlled either internally by sensor devices mounted within the patient or externally by means of signals transmitted electromagnetically from an external control device.

The pump as described delivers very small quantities of fluid, as shown about 0.1 micro liters per pump sample. The advantages of the pump as described are its very small size and its cheapness as compared with peristaltic pumps or solenoid pumps and pump is therefore very suitable for applications where accurate quantities of liquid must be pumped in small amounts and where a pump of small size is required.

We claim:
1. A dispensing device, comprising:
   a housing forming a reservoir for fluid to be dispensed and a pump for dispensing the fluid located within the reservoir;
   said pump including a pump chamber, a movable pump element and a piezoelectric element, said pump element being physically contiguous with and directly coupled to said piezoelectric element whereby changes in dimension of said piezoelectric element induce pumping movement in the movable pump element;
   a source of electrical power connected to a control means for cyclically applying electrical voltage to said piezoelectric element for inducing periodic changes in dimension in said piezoelectric element;
   a first one-way valve member bing directly connected between the fluid reservoir and the pump chamber for permitting flow of a fluid from said reservoir into said pump chamber upon movememt of the pump element and a second one-way valve member connected between the pump chamber and an outlet for dispensing said fluid from said pump chamber; and
   means for maintaining the pressure of the fluid in the reservoir as the fluid is being dispensed, said pressure maintaining means including an expandable member having one end connected to said pump which closes a space defined by said expandable member.

2. A dispensing device according to claim 1, wherein said movable pump element comprises a flexible diaphragm forming a part of the wall of said pump chamber.

3. A dispensing device according to claim 1, wherein the source of electrical power is a battery in the shape of a disc and the control menas in the shape of a planar member, wherein the battery, control circuit and pump chamber are stacked upon one another to form a disc-like pump configuration.

4. A dispensing device according to claim 2, wherein the source of electrical power is a battery in the shape of a disc and the control means in the shape of a planar member, wherein the battery, control circuit and pump chamber are stacked upon one another to form a disc-like pump configuration.

5. A dispensing device according to claim 1, wherein said control means includes receiver means responsive to remotely transmitted electromagnetic waves for actuating said pump.

6. A dispensing device according to claim 2, wherein said control means includes receiver means responsive to remotely transmitted electromagnetic waves for actuating said pump.

7. A dispensing device according to claim 5, further comprising means for checking the condition of the source of electrical power.

8. A dispensing device according to claim 1, comprising an inlet chamber connected to said reservoir and sealed by an elastomeric member for permitting injection of the fluid into said reservoir by means of a hypodermic syringe.

9. A dispensing device according to claim 1, wherein said expandable member is a bellows.

* * * * *